(12) United States Patent
Klein

(10) Patent No.: US 8,506,551 B2
(45) Date of Patent: Aug. 13, 2013

(54) INFILTRATION CANNULA

(76) Inventor: Jeffrey A. Klein, San Juan Capistrano, CA (US)

( * ) Notice: Subject to any disclaimer, the term of this patent is extended or adjusted under 35 U.S.C. 154(b) by 0 days.

(21) Appl. No.: 13/189,775

(22) Filed: Jul. 25, 2011

(65) Prior Publication Data

US 2011/0282323 A1    Nov. 17, 2011

Related U.S. Application Data

(63) Continuation of application No. 11/800,355, filed on May 4, 2007, now Pat. No. 8,105,310, which is a continuation-in-part of application No. 10/877,566, filed on Jun. 25, 2004, now abandoned, which is a continuation-in-part of application No. 10/442,370, filed on May 21, 2003, now abandoned.

(51) Int. Cl.
*A61M 31/00*    (2006.01)

(52) U.S. Cl.
USPC .................. 604/506; 604/512; 604/164.01

(58) Field of Classification Search
USPC .................. 604/164.01, 506, 512, 171, 187, 604/239, 272, 542
See application file for complete search history.

(56) References Cited

U.S. PATENT DOCUMENTS

| | | | |
|---|---|---|---|
| 2,708,437 A | 5/1955 | Hutchins |
| 3,082,805 A | 3/1963 | Royce |
| 3,732,858 A | 5/1973 | Banko |
| 3,734,099 A | 5/1973 | Bender |
| 3,955,579 A | 5/1976 | Bridgman |
| 3,994,297 A | 11/1976 | Kopf |
| 4,167,944 A | 9/1979 | Banko |
| 4,203,444 A | 5/1980 | Bonnell et al. |
| 4,311,140 A | 1/1982 | Bridgman |
| 4,314,560 A | 2/1982 | Helfgott et al. |
| 4,405,322 A | 9/1983 | Jessup |
| 4,460,360 A | 7/1984 | Finegold |
| 4,487,600 A | 12/1984 | Brownlie et al. |
| 4,530,356 A | 7/1985 | Helfgott et al. |
| 4,536,180 A | 8/1985 | Johnson |
| 4,577,629 A | 3/1986 | Martinez |
| 4,586,921 A | 5/1986 | Berson |
| 4,589,414 A | 5/1986 | Yoshida et al. |
| 4,713,053 A | 12/1987 | Lee |

(Continued)

FOREIGN PATENT DOCUMENTS

FR       2777462       10/1999

OTHER PUBLICATIONS

Jeffrey Alan Klein, MD; The Tumescent Technique Anesthesia and Modified Liposuction Technique Dermatologic Clinic; vol. 8, No. 3, Jul. 1990.

(Continued)

*Primary Examiner* — Laura Bouchelle
(74) *Attorney, Agent, or Firm* — Stetina Brunda Garred & Brucker

(57) ABSTRACT

An infiltration cannula and method of using the infiltration cannula during a tumescent infiltration procedure are disclosed herein. The infiltration cannula may have an outwardly flaring hub which may be wedged into an adit of a patient to minimize leakage of fluid being infiltrated into the patient. Also, the infiltration cannula may be utilized to hydrate a dehydrated patient by a medically untrained person. The infiltration cannula may also be used to deliver an antibiotic/vasoconstrictive drug solution to minimize surgical site infections.

2 Claims, 4 Drawing Sheets

(56) References Cited

U.S. PATENT DOCUMENTS

| | | | |
|---|---|---|---|
| 4,735,605 A | 4/1988 | Swartz | |
| 4,775,365 A | 10/1988 | Swartz | |
| 4,784,649 A | 11/1988 | Imonti et al. | |
| 4,790,830 A | 12/1988 | Hamacher | |
| 4,815,462 A | 3/1989 | Clark | |
| 4,850,354 A | 7/1989 | McGurk-Burleson et al. | |
| 4,886,491 A | 12/1989 | Parisi et al. | |
| 4,919,129 A | 4/1990 | Weber, Jr. | |
| 4,925,450 A | 5/1990 | Imonti et al. | |
| 4,932,935 A | 6/1990 | Swartz | |
| 4,938,743 A | 7/1990 | Lee | |
| 5,052,999 A | 10/1991 | Klein | |
| 5,112,302 A | 5/1992 | Cucin | |
| 5,181,907 A | 1/1993 | Becker | |
| 5,186,714 A | 2/1993 | Boudreault et al. | |
| 5,203,769 A | 4/1993 | Clement et al. | |
| 5,236,414 A | 8/1993 | Takasu | |
| 5,242,386 A | 9/1993 | Holzer | |
| 5,244,458 A | 9/1993 | Takasu | |
| 5,286,253 A | 2/1994 | Fucci | |
| 5,295,980 A | 3/1994 | Ersek | |
| 5,314,407 A | 5/1994 | Auth | |
| 5,348,535 A | 9/1994 | Cucin | |
| 5,352,194 A | 10/1994 | Greco et al. | |
| 5,446,070 A | 8/1995 | Mantelle | |
| 5,447,493 A | 9/1995 | Blugerman et al. | |
| 5,453,088 A | 9/1995 | Boudewijn et al. | |
| 5,472,416 A | 12/1995 | Blugerman et al. | |
| 5,489,291 A | 2/1996 | Wiley | |
| 5,514,086 A | 5/1996 | Parisi | |
| 5,643,198 A | 7/1997 | Cucin | |
| 5,655,544 A | 8/1997 | Johnson | |
| 5,665,100 A * | 9/1997 | Yoon | 606/170 |
| 5,725,495 A | 3/1998 | Strukel et al. | |
| 5,795,323 A | 8/1998 | Cucin | |
| 5,800,407 A | 9/1998 | Eldor | |
| 5,807,282 A | 9/1998 | Fowler | |
| 5,817,050 A | 10/1998 | Klein | |
| 5,884,631 A | 3/1999 | Silberg | |
| 5,947,988 A | 9/1999 | Smith | |
| 5,968,008 A | 10/1999 | Grams | |
| 6,020,196 A | 2/2000 | Hu et al. | |
| 6,022,362 A * | 2/2000 | Lee et al. | 606/159 |
| 6,039,048 A | 3/2000 | Silberg | |
| 6,071,260 A | 6/2000 | Halverson | |
| 6,102,885 A | 8/2000 | Bass | |
| 6,113,569 A | 9/2000 | Becker | |
| 6,129,701 A | 10/2000 | Cimino | |
| 6,162,202 A | 12/2000 | Sicurelli et al. | |
| 6,238,355 B1 | 5/2001 | Daum | |
| 6,280,424 B1 | 8/2001 | Chang et al. | |
| 6,375,648 B1 | 4/2002 | Edelman | |
| 6,428,499 B1 | 8/2002 | Halverson | |
| 6,436,116 B1 | 8/2002 | Spitz et al. | |
| 6,524,300 B2 | 2/2003 | Meglin | |
| 6,613,026 B1 | 9/2003 | Palasis et al. | |
| 6,685,666 B1 | 2/2004 | Fontenot | |
| 6,692,473 B2 | 2/2004 | St. Cyr et al. | |
| 6,706,026 B1 | 3/2004 | Goldstein et al. | |
| 6,916,292 B2 | 7/2005 | Morawski et al. | |
| 6,969,373 B2 | 11/2005 | Schwartz et al. | |
| 7,056,315 B2 | 6/2006 | Gonon | |
| 7,465,291 B2 | 12/2008 | Massengale | |
| 2004/0215143 A1 | 10/2004 | Brady et al. | |
| 2004/0236313 A1 | 11/2004 | Klein | |
| 2006/0259111 A1 | 11/2006 | Peterson | |

OTHER PUBLICATIONS

Jeffrey A. Klein, M.D.; "The Tumescent Technique for Lipo-Suction Surgery", The American Journal of Cosmetic Surgery; vol. 4, No. 4, 1987.

Jeffrey A. Klein, M.D.; "Tumescent Technique for Regional Anesthesia Permits Lidocaine Doses of 35 mg/kg for Liposuction"; J. Dermatol. Surg. Oncol 16:3; Mar. 1990.

Jeffrey A. Klein, M.D.; "Tumescent Technique for Local Anesthesia Improves Safety in Large-Volume Lipsuction"; The American Society of Plastic and Reconstructive Surgeons; Nov. 1993.

"Patient-Controlled Transdermal Fentanyl Hydrochloride vs. Intravenous Morphine Pump for Postoperative Pain" article in JAMA, Mar. 17, 2004—vol. 291, No. 11 (9 pages).

* cited by examiner

INFILTRATION CANNULA

CROSS-REFERENCE TO RELATED APPLICATIONS

The present application is a continuation of U.S. patent application Ser. No. 11/800,355, filed May 4, 2007, which is a continuation-in-part application of pending U.S. Ser. No. 10/877,566, filed Jun. 21, 2004, which is a continuation-in-part application of Applicant's prior U.S. Ser. No. 10/442,370 filed May 21, 2003 entitled INFILTRATION CANNULA, and is related to U.S. patent application Ser. No. 10/877,337, filed Jun. 25, 2004 now U.S. Pat. No. 7,572,613, issued on Aug. 11, 2009, the disclosures of which are expressly incorporated herein by reference.

STATEMENT RE: FEDERALLY SPONSORED RESEARCH/DEVELOPMENT

Not Applicable

BACKGROUND OF THE INVENTION

The present invention relates in general to an infiltration cannula permitting the infiltration of very large volumes of tumescent fluid in a safe and painless manner.

Definitions:

infiltration: an injection that causes a fluid to permeate or percolate through pores or interstices. Thus an infiltration refers to an injection directly into tissue.

infusion: an injection that pours a fluid into a place or into (the lumen of a blood) vessel. Thus an infusion refers to an intravascular injection.

injection: The action of forcing a fluid, etc. into tissue or cavity, as by means of a syringe, or by some impulsive force.

Tumescent Technique, Tumescent Infiltration: The tumescent technique is a method of subcutaneous drug delivery of large volumes of very dilute medication together with dilute epinephrine in isotonic solution of crystalloid (e.g. physiologic saline, lactated Ringer's solution, Hartman's solution, etc) infiltrated directly into subcutaneous fat or muscle or along the exterior length of a vein to produce swelling and firmness, or tumescence, of the targeted tissues, and thus produce very slow systemic absorption as a result of intense subcutaneous vasoconstriction, as well as direct hydrostatic compression of capillaries and veins.

Tumescent Drug Delivery, Tumescent Delivery: Tumescent drug delivery and synonyms refer to the tumescent technique for delivering a drug into the subcutaneous space. In other words, tumescent delivery is a process of infiltration of very large volumes of very dilute solutions of therapeutic substances dissolved in a crystalloid solution into subcutaneous tissue to the point of producing tumescence of the targeted tissue. Drugs other than lidocaine can be administered by means of tumescent delivery, that is, by subcutaneous infiltration of extremely dilute drug, with or without a vasoconstrictor such as epinephrine.

Tumescent Local Anesthesia (TLA) is local anesthesia produced by direct infiltration into subcutaneous tissue of large volumes of very dilute lidocaine (e.g., less than or equal to 1 gram/liter) and epinephrine (e.g., less than or equal to 1 milligram/liter) with sodium bicarbonate (e.g., 10 milliequivalents/liter) in a crystaloid solution such as physiologic saline (NaCl) or lactated Ringer's solution. Although higher concentrations can be used and still qualify as TLA, it is generally safer to use the least (lowest) effective concentration.

Tumescent Local Anesthetic Solution (TLA Solution) is the local anesthetic solution used to produce TLA. Typically, a TLA Solution consists of a 10 to 20 fold dilution of commercially available concentration of lidocaine and epinephrine. Thus, a commercial solution of lidocaine and epinephrine contains 10 grams of lidocaine per liter (10 gm/L) and 10 milligrams of epinephrine per liter. In contrast TLA Solution typically contains very dilute lidocaine ($\leq 1$ gram/liter) and epinephrine ($\leq 1$ milligram/liter) with sodium bicarbonate (10 milliequivalents/liter) in a crystalloid solution such as physiologic saline or lactated Ringer's solution. Typically the volume of infiltrated TLA Solution is so large that the skin and subcutaneous tissue becomes tumescent, in other words swollen and firm.

tumescent, tumescence: swollen and firm tumescent liposuction: liposuction performed totally by local anesthesia using tumescent local anesthesia.

tumescent fluid, tumescent solution: dilute solutions of therapeutic substances dissolved in a crystalloid solution intended for tumescent delivery into subcutaneous tissue.

tumescent "drug": the "drug" in the context as an ingredient in a tumescent solution and its pharmacokinetic behavior as a result of the pharmacokinetics of a tumescent solution; for example tumescent lidocaine, tumescent epinephrine, tumescent antibiotic.

Tumescent Pharmacokinetics: The absorption pharmacokinetics (the pharmacologic and physiologic factors associated with the systemic absorption of a drug) after tumescent infiltration of a drug is dramatically slower than the rate of systemic absorption of routine injection of the drug. The intense vasoconstriction induced by epinephrine, slows the rate of drug absorption into the central circulation and prolongs the local effects of the drug. For example, the duration of routine local anesthesia with lidocaine is typically 2 hours, in contrast the duration of local anesthesia with tumescent local anesthesia may be 12 to 18 hours or more. A similar prolonged effect of tumescent antibiotic infiltration significantly improves the prophylactic effect of preoperative antibiotic therapy in the prevention of surgical site infections.

adit: a small round hole in the skin (typically 1 mm, 1.5 mm or 2 mm diameter) made by a skin-biopsy punch, and intended to be an access port for percutaneous entry into the subcutaneous fat by a tumescent infiltration cannula and/or a liposuction cannula.

Many medical procedures require infiltration of fluids, such as a local anesthetic. For example, liposuction may be performed entirely by tumescent local anesthesia which was invented by Jeffrey A. Klein. Dr. Klein first published the description of tumescent local anesthesia to perform liposuction in 1987 (Klein J A. The tumescent technique for liposuction surgery. J Am Acad Cosmetic Surg 4:263-267, 1987). The tumescent technique was invented in order to eliminate the dangers of liposuction surgery under general anesthesia and the associated excessive bleeding. With proper technique, tumescent infiltration permits liposuction totally by local anesthesia with virtually no surgical blood loss.

One method of infiltration of local anesthetic is via a blunt tipped infiltration cannula. Infiltrators are known as sprinkler-tip or Klein™ (the present applicant) needle infiltrators. These cannulas are constructed out of a rigid stainless steel and have one or more apertures, which are typically round or oval, and are distributed about the distal end of the cannula. The apertures are distributed over about 15% to 25% or less than 5.0 cm. of the distal end of the cannula needle. These traditional infiltration cannulas are intended to be inserted through a small incision in the patient's skin and then moved in and out through the subcutaneous tissue while a dilute solution of local anesthetic (or other pharmaceutical solution) is ejected through the distal apertures. Since the cannula needle is moved in and out, only the distal end (e.g., about 15% to 25%) of the cannula needle may have apertures. Otherwise, fluid may squirt out of the apertures and onto medical professionals when the cannula needle is moved out too much. Such infiltrators typically have a blunt tip and require the placement of a small hole (made by a one mm skin-biopsy punch or a small surgical blade) through which the blunt tipped cannula can be passed. Unfortunately, the piston-like in and out motion of the cannula causes the patient discomfort.

Another type of infiltration cannula is the sharp tipped tumescent infiltration cannula which is available as 1) a single long sharp needle similar to a spinal needle and 2) a group of short sharp hypodermic needles each connected by separate plastic tube to a manifold that distributes TLA solution. The first type of needle is inserted into subcutaneous fat and infiltration proceeds while the needle is continuously moved in and out along paths that radiate from the skin puncture site. A targeted area is eventually anesthetized after multiple skin punctures. The second type, the group of short sharp needles, consists of a group of individual hypodermic needles each attached to an individual IV extension tube, which are in turn connected to a multi port manifold which connected to a reservoir (IV bag) of tumescent fluid. These sharp-tipped tumescent infiltration devices have been associated with puncture-injury to deeper tissues such as the lungs causing pneumothorax or intra-abdominal viscera causing peritonitis.

In summary, there are two causes of pain associated with the blunt and sharp tipped infiltration cannulas. One significant cause of pain is a continuous in and out motion of the cannula as it moves through non-anesthetized tissue. In order to deliver tumescent anesthetic solution throughout an entire compartment of subcutaneous fat, the anesthetist must move the cannula with a continuous to and fro reciprocating motion, and repeatedly change directions. Each advance of the cannula through fat causes discomfort and pain. The second cause of pain is associated with an excessively rapid distention of tissue resulting from a high rate of fluid injection into a relatively small volume of tissue via limited number of holes on the distal tip of the infiltration cannula. Ironically, the pain associated with each of these two factors often necessitates the use of narcotic analgesia, IV sedation, or general anesthesia in order to infiltrate local anesthesia. The present invention eliminates or greatly reduces these two sources of pain.

Another method of fluid insertion is via a peripherally inserted central catheter, also called a PICC line comprising an elongate plastic tube that is placed inside a vein of the patient. PICC lines are typically used for procedures requiring delivery of fluids over a prolonged period of time. For example, a PICC line may be used when a patient needs to receive intravenous (IV) fluids, such as medication or nutrients over a prolonged period of time, such as a week or more.

The On-Q® Pain Management System marketed by I-Flow® Corporation employs a flexible plastic or silicone catheter system for continuously providing local anesthetic. This system provides prolonged local anesthesia by means of an elastomeric (elastic container) device that continuously infiltrates a solution of local anesthesia over many hours. The On-Q® device comprises a long soft flexible tube with many small holes arranged along a significant portion of the tube. The On-Q® device is designed to be initially positioned within a surgical wound at the time of surgery. After the surgical wound is closed, the On-Q® device permits slow steady infiltration of a local anesthetic solution into the wound, thereby attenuating post-operative pain. The On-Q® device cannot be inserted through a tiny hole in the skin into subcutaneous tissue. Therefore the On-Q device cannot achieve infiltration of local anesthesia and prevent post-operative pain in a preemptive fashion. It has been shown that preemptive local anesthesia in the form of peripheral nerve blocks, can prevent nocioception by the central nervous system (CNS) during general anesthesia, and thereby prevent chronic post-operative pain syndromes similar to "phantom-limb syndrome." Thus there is a need for a simple device that can permit the direct percutaneous insertion of a multi-holed infiltration cannula into subcutaneous tissue for the localized delivery of medications such as local anesthetics, chemotherapeutic agents, or crystalloids for parenteral hydration.

Traditional techniques for subcutaneous injection of local anesthetic solutions (e.g. peripheral nerve blocks) use a high-concentration/low-volume of local anesthetic. This is associated with a rapid systemic absorption of the local anesthetic. In order to achieve a prolonged local anesthetic effect, the traditional techniques for using local anesthetics necessitate either frequent repeated injections or slow continuous subcutaneous infusion of the local anesthetic. As described above, repeated injections or piston-like movement of the cannula causes patient discomfort. Slow continuous infiltration may not be desirable in certain situations. Furthermore, continuous infiltrations restrict patient movement for extended periods of time which also cause the patient discomfort. Thus, there is a need for a system for infiltration of a local anesthetic into intact subcutaneous tissue (not necessarily into peri-incisional tissue) which decreases patient discomfort pre-emptively, and allows prolonged local anesthesia either by rapid (less than 10 to 15 minutes) bolus injections, extended infiltration (e.g. over intervals ranging from 15 minutes to several hours) or continuous slow infiltration over many hours to days. Furthermore there is a need for a devise that can provide pre-emptive local anesthesia before a surgical wound is created. There is also a need for a percutaneously-insertable infiltration cannula, with applications that are unrelated to the delivery of local anesthesia, which can be easily inserted by rescuers with minimal clinical skill or training. One example is the need for a cannula that permits emergency fluid resuscitation in situations where an IV cannot be established such as nighttime military combat conditions where using a flash light to establish an IV access would be extremely dangerous. Another example is the need to provide emergency fluid resuscitation to large numbers of patients in acute epidemic diarrhea (dehydration) associated with biological warfare, or mass-trauma situations such as a natural disaster (earth quake) or terrorist attack. There is also a need for a device that can easily provide localized fluid resuscitation to burn victims whereby fluid is infiltrated into the subcutaneous tissue directly subjacent to burned skin.

Other types of devices for delivering fluid to a patient exist in the prior art. For example, U.S. Pat. Pub. No. 2003/0009132 (Schwartz et al.) is directed to a micro-intravascular (never extra-vascular) catheter for infusing milliliter quantities of drugs for the lysis of intravascular blood clots (i.e., a micro target). Another embodiment of the Schwartz device is intended to improve the precision and safety of intra-myocardial delivery of micro-liter volumes of fluid for biologic gene therapy based angiogenesis.

Unfortunately, the Schwartz device requires a sterile high tech hospital environment and demands fluoroscopy and ultrasound guidance. The Schwartz device requires a highly trained, experienced and skilled medical professional to operate. In particular, the Schwartz infiltration catheter is defined by its obligatory guidewire and intravascular target. The intravascular insertion of the catheter via the guidewire is a complex procedure that requires significant clinical training, experience and skill. Specifically, it involves 1) preparation with a sterile surgical field, 2) making a skin incision and inserting an introducing catheter having coaxial stylet into the targeted vessel, 3) removing the stylet, 4) inserting the guidewire through the introducing catheter and into the vessel, 5) withdrawing the introducing catheter from the vessel without disturbing the intravascular location of the guidewire, 6) slipping the distal tip of the infiltration catheter over the proximal end of the guidewire, and advancing the infiltration catheter over the considerable length of the guidewire through the skin and into the intraluminal space of the targeted vessel, 7) withdrawing the guidewire and attaching the proximal end of the infiltration catheter to a source of the therapeutic fluid to be delivered into the targeted vessel. This insertion procedure is so specialized that a majority of physicians do not have the requisite expertise to qualify for hospital privileges for inserting an intravascular catheter using a guidewire. Locating a clotted blood vessel and inserting the Schwartz catheter into the vessel requires the ultrasound guidance.

As understood, an important feature of the Schwartz device is the shape, size, direction and pattern of the holes on the infiltration cannula. As stated in paragraph 15 of the Schwartz disclosure, "there is a need for an injection device that gives control over the concentration, pattern, and location of the deposition of an injectate." The Schwartz device is intended to improve directional control over the direction of injection of minute volumes of injectate.

The Schwartz device appears to be specifically designed to avoid vascular compression. For the small needle embodiment of Schwartz, vascular compression resulting from injecting excessive volume of drug into myocardium may precipitate infarction or arrhythmia. Likewise, for the long cannula embodiment of Schwartz vascular compression appears to be contraindicated. The goal of infusing fluid into a vessel containing a blood clot is to open the vessel, and not compress it.

The Schwartz device also appears to be incapable of large volume (e.g., multi liter) subcutaneous infiltration. The long plastic Schwartz catheter appear to be specifically intended for intravascular use. Moreover, Schwartz cannula cannot have holes distributed along 100% of its entire length based on a contention that such situation will lead to a contradictory situation. If the Schwartz device does have holes along its entire length then either the entire length of the cannula would have to be positioned inside a vessel (unlikely without attaching the cannula proximally to another catheter in which case the bulky attachment mechanism would have to be passed through the wall of the vessel) or else some of the holes would have an extravascular location (unlikely because the therapeutic fluid would either leak onto the patient's skin or extravasate into the perivascular and subcutaneous tissues). In either case, the potential for serious adverse effects would be significant.

Moreover, the Schwartz device does not appear to be capable of being reciprocated in and out of the subcutaneous tissue of the patient to locally anesthetize an entire compartment.

In summary, the Schwartz infiltrator is intended for 1) intravascular insertion which demands a complex guidewire procedure involving several steps, 2) intravascular drug delivery (for lysis of blood clots) or intra myocardial injections, 3) injection of a miniscule volume (micro liters) of drug.

Another type of device for delivering fluid to a patient is described in U.S. Pat. No. 6,524,300, issued to Meglin. Similar to the Schwartz device, the Meglin device appears to be an intravascular device intended to inject a "medical agent into the target lumen of the body." (see Col. 2, lns. 41-48). Meglin is specifically intended to be inserted intralumenally into "a lumen of a blood vessel or another cavity within a patient's body." (see Col. 1, lns. 14-19). This is precisely opposite the goal of a tumescent infiltration cannula. A tumescent infiltration cannula is intended to deliver drugs to the subcutaneous space which excludes the vascular space and cavitary space. As such, the Meglin device appears to be specifically designed to avoid vascular compression and to not induce vasoconstriction. An important aspect of the Meglin device appears to be the size and density of the apertures to control the rate of flow of fluidic medication. Moreover, it appears that the medical professional utilizing the Meglin device requires a great deal of training, expertise and education based on a contention that the infusion segment of the device is located intravascularly by locating a radiopaque marker band with a fluoroscopy.

Another type of device for delivering fluid to a patient is described in U.S. Pat. No. 6,375,648, issued to Edelman, et al. Similar to prior art blunt or sharp tipped infiltration cannulas, the apertures are restricted to the distal 25% of the cannula. The reason is that otherwise, the fluidic medication would squirt out of the apertures and contaminate the operating room. Col. 2, lns. 22-25 states that "once within the tissue of a patient a treatment solution may be infused into the tissue by working the cannula 20 through the fat tissue of the patient." As understood, the Edelman device suffers from the same deficiencies discussed above in relation to the blunt or sharp tipped infiltration cannulas. The Edelman cannula is reciprocated in and out of the subcutaneous tissue, and thus, causes pain or discomfort to the patient. Moreover, the only novel aspect of Edelman appears to be the cannula's Teflon coating.

Surgical site infections are a significant source of postoperative morbidity and mortality. They account for 17% of all hospital acquired infections, require prolonged hospital stays and contribute substantially to health care costs. The incidence of surgical site infection is a function of the type of surgical procedure, the surgeon, and the hospital. The risk of SSI is significantly associated with a number of factors including anesthetic risk scores, wound class and duration of surgery.

The true incidence of SSI is probably higher than what has been reported in the literature. The primary surgical team is often not aware of incisional infections diagnosed after hospital discharge. Patients who had SSI diagnosed after discharge require substantially more outpatient visits, emergency visits, radiology services and home healthcare services. A study published in 2004 found such infections cost $6,200 per patient for home care expenses associated with wound care. The major sources of infection are microorganisms on the patient's skin. A number of preoperative skin care techniques have been used to limit concentrations of bacteria at the surgical site, including antiseptic preparations, adhesive barrier drapes, topical antibiotics, hair removal and hand hygiene.

Antimicrobial prophylaxis with intravenous (IV) antibiotics is currently the most important clinical modality for preventing SSI. The consensus recommendation for antimicrobial prophylaxis is for antimicrobial agents to be given as an IV infusion of antibiotics to be given within the first 60 minutes before surgical incision and that prophylactic antimicrobial agents be discontinued within 24 hours of the end of surgery.

Recent Center for Disease Control (CDC) guidelines for antimicrobial prophylaxis do not mention preoperative perilesional infiltration of antibiotics (http://www.cdc.gov/ncidod/dhqp/pdf/guidelines/SSI.pdf). A recent review of surgical site infections only discussed intravenous (IV) delivery of prophylactic antibiotics. The possibility of preoperative peri-incisional infiltration to prevent SSI was not considered.

Several studies of SSI in the 1980's compared the effectiveness of antimicrobial prophylaxis by IV infusion or by peri-incisional infiltration. A 1981 study of the incidence of wound infection among 405 abdominal surgery patients found no significant difference between 1 gm of cephaloridine given intravenously or intra incisional at the end of the surgery. Following this trial, IV antibiotics at the induction of anesthesia became standard practice.

An IV infusion of fluid is a common medical procedure to treat patients. Unfortunately, an IV infusion is associated with an inherent expense, difficulty and risk. There are also unfortunately times when an IV line cannot be established in the patient. By way of example and not limitation, the patient may be burned such that a vein of the patient cannot be located to establish an IV access. The patient may have been traumatized in such a way that will not allow a doctor to perform an IV cut down procedure. Additionally, the patient may be very obese such that the vein of the patient is difficult to locate. In other situations, occurring in remote locations where a trained medical professional is not available to establish the IV such as the international space station or on an airplane. Currently, there does not appear to be any in flight capability for treating an acute traumatic injury on a plane or on the space shuttle. If the pilot or astronaut survives the immediate effects of an explosion, burn, or decompression injury, or if there is an acute non-traumatic medical illness, it is assumed that the victim must return to terra firma for any significant therapeutic intervention such as providing systemic fluid replacement. Other situations include a mass casualty situation where there are insufficient number of trained medical professionals compared to the number of victims/patients, etc.

Other methods of delivering a drug to a patient other than an IV infusion may be oral delivery of the drug. Unfortunately, oral delivery of the drug results in inconsistent absorption of the drug into the gastrointestinal tract. The drug may alternatively be delivered via periodic intramuscular injections. Unfortunately, the fluidic drug serum may have varying levels of concentration at each of the periodic injections.

BRIEF SUMMARY OF THE INVENTION

The present invention addresses the needs discussed above, identified below and those that are known in the art.

An infiltration cannula and method of using the infiltration cannula during an infiltration procedure is discussed herein. The infiltration cannula preferably includes: a flexible cannula, a hub, and a rigid stylet. The flexible cannula has a proximal end and a distal end. The flexible cannula also has a plurality of apertures disposed in a pattern about the distal end. The apertures are configured to infiltrate fluid into the subcutaneous tissue of a patient. The hub is configured to be held by a person performing the infiltration procedure. The hub has a first end and an opposing second end. The first end is attached to the proximal end of the flexible cannula and the second end includes a connector configured to connect to an input source for receiving the fluid to be infiltrated into the subcutaneous tissue of the patient. The fluid flows from the connector, through the hub and into the flexible cannula.

The flexile cannula may be manufactured of plastic and the rigid stylet may be fabricated from stainless metal or rigid plastic. The distal end of the cannula is closed to cover the tip of the rigid stylet or open with a hole allowing the tip of the rigid stylet to protrude through. The tip of the rigid stylet is either sharp to directly insert through the skin of the patient, or so blunt that a skin incision is required to permit insertion of the rigid stylet and the cannula into the subcutaneous space. The stylet may be formed to have either a solid or hollow cross-sectional configuration. The hollow rigid stylet may have small holes distributed along its length in a pattern dissimilar or identical to the pattern of holes placed along the flexible cannula into which the stylet is inserted. Thus the stylet itself can be used as an infiltration cannula.

The apertures may be arranged in a helical pattern or in a spiral pattern.

The apertures may be distributed over about 33% to about 100% of the distal end of the tubular needle.

The apertures may be round or oval. The size of the apertures need not necessarily be equal.

The fluid may comprise a local anesthetic or any other therapeutic solution.

The infiltration procedure may be performed in conjunction with conventional medical procedures such as liposuction, but additionally may simply be used as a mode of systemic drug delivery, or systemic fluid replacement therapy.

A method of infiltrating fluid into subcutaneous tissue of a patient using an infiltration cannula, such as the one described above may include the following steps.

A rigid stylet is inserted through a flexible infiltration cannula. The infiltration cannula is inserted through a patient's skin and into the subcutaneous tissue or muscle tissue of the patient at a desired site with the stylet providing rigidity to the flexible cannula during the insertion process. After the stylet is withdrawn from the cannula, a fluid is provided from a fluid source via the connector. The fluid is transported from the connector through the hub and into the flexible cannula. The fluid is ejected from the cannula into the subcutaneous tissue or muscle of the patient via the apertures.

The infiltration cannula used in performing the method preferably includes a connector for receiving the fluid from a fluid source, a hub in communication with the connector and a flexible cannula in communication with the hub. The tubular needle has a plurality of apertures disposed in a pattern about a distal end. The apertures are configured to infiltrate the fluid into the subcutaneous tissue or muscle of the patient.

The above steps may be repeated intermittently, at intervals between a few minutes to many hours.

After the desired amount of fluid has been infiltrated at a given site, the infiltration cannula may be removed or may remain in place for possible additional infiltration.

The infiltration cannula may additionally be inserted at a new site.

Multiple infiltration cannulas (e.g., two) may be used simultaneously. Use of multiple infiltration cannulas prevents disruption of the infiltration process when one infiltration cannula is removed and relocated. In particular, a second infiltration cannula may be inserted closely adjacent to a first infiltration cannula which has partially anesthetized the area in which the second infiltration cannula is being inserted to reduce the pain associated with inserting the second infiltration cannula into non anesthetized tissue. Multiple infiltrators can be simultaneously inserted into separate areas to facilitate more rapid delivery of fluids.

The infiltration cannula discussed herein may provide for (1) a simple subcutaneous insertion, (2) either regional drug delivery directly into subcutaneous tissues or systemic drug when intravascular access is not possible, and (3) infiltration of very large volumes (e.g., multi liters) of tumescent fluid. The infiltration cannula discussed herein allows tumescent infiltration with less pain and greater safety.

In an aspect of the cannula, the same may be used to prevent or minimize surgical site infections. For example, a solution of epinephrine, an antibiotic drug, and optionally, lidocaine may be administered to a surgical site.

BRIEF DESCRIPTION OF THE DRAWINGS

These as well as other features of the present invention will become more apparent upon reference to the drawings wherein.

DETAILED DESCRIPTION OF THE INVENTION

Figure 1:
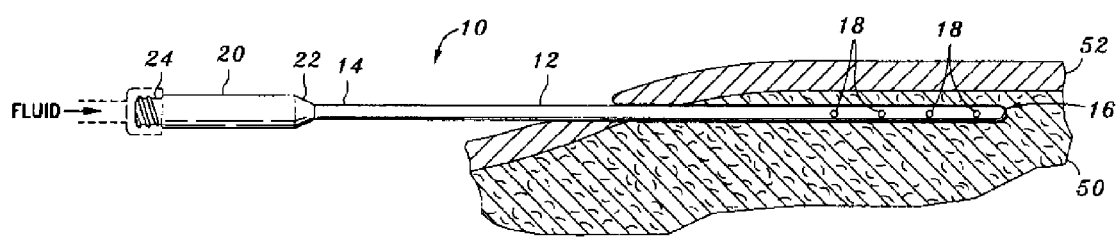
FIG. 1 is a side elevation view of a stainless steel infiltration cannula with a closed tip shown inserted in subcutaneous tissue shown in partial cross section.

As described in further detail below, the present invention takes advantage of the tumescent technique in order to provide intermittent or continuous, brief or prolonged multi-liter infiltration of local anesthetic, physiologic fluid, antibiotics or other therapeutic solution with a significant decrease in patient discomfort due to the elimination of the piston-like in and out motion of the cannula. Once the cannula is positioned in place, there is no need to repeatedly move the cannula in and out through the tissue in order to deliver the fluid to a wide area. Using the tumescent technique and stainless steel versions of the present invention, the time needed in order to complete the infiltration of a targeted anatomic area is reduced to nearly half of the time required when using traditional prior art cannulas. The device and method of the present invention can use multiple (e.g., two or more) infiltration cannulas simultaneously. While one cannula is actively dispersing tumescent fluid into the subcutaneous tissue, the surgeon can reposition a second infiltration cannula. This allows the infiltration process to proceed without interruption, whereas prior art techniques of infiltration must be ceased each time the cannula is withdrawn from the skin and re-inserted into another direction.

The flexible plastic cannula version of the present invention provides a means for relatively rapid fluid resuscitation in emergency situations such as when establishing an intravenous (IV) access is not feasible. A large volume of a tumescent crystalloid solution to treat intravascular fluid deficit may be delivered subcutaneously when an intravascular (IV) line cannot be started for fluid replacement. (e.g., remote area, obese patient, burn/trauma victim, unavailable trained medical professional, etc.). As a further refinement, rapid systemic absorption of physiologic saline can be achieved by adding a vasodilator drug to saline and using the tumescent technique to deliver the solution into subcutaneous tissue. For example, in the setting of overwhelming mass casualties where there is no hope or expectation of trained clinical personnel being available, the ability of untrained first-responders to provide immediate fluid resuscitation could save many lives. When a disaster causes an overwhelming number of trauma or burn victims, or when a cholera epidemic leaves victims with life-threatening dysentery and dehydration, it is unlikely that there will be sufficient trained personnel to start an IV line for IV fluid resuscitation. In such a setting, anyone (e.g., adult of average intelligence with minimal clinical training), perhaps even a victim himself, could simply insert one or more disposable plastic infiltration cannulas directly through the skin on the thigh(s) and into subcutaneous tissue and attach an IV bag and then allow the force of gravity to propel the fluid into the subcutaneous space in a tumescent fashion. The resulting systemic absorption and redistribution into the intracellular and intravascular compartments could be life-saving. This emergency resuscitation procedure relies on the combination of 1) the plastic-catheter embodiment and 2) absorption kinetics of tumescent fluid delivered to subcutaneous tissue.

The flexible cannula may also have important applications as in treating a wounded soldier in night-time combat conditions when establishing an IV access in total darkness is nearly impossible or using a flash light might attract enemy fire. The flexible cannula may similarly have important applications in other areas of use such as treating mass-casualty victims suffering hypovolemia as a result of epidemic infections, biologic warfare, or trauma such as explosions, burns or radiation exposure. The flexible cannula similarly has applications in surgical patients wherein the surgeon can provide localized pre-operative preemptive analgesia and simultaneously provide tumescent delivery of a prophylactic dose of an antibiotic aimed precisely at tissues targeted for surgical intervention.

As is well known, the tumescent technique was discovered by Jeffrey Alan Klein, M.D. (the present applicant) in 1985. Dr. Klein first published a description of the tumescent technique in 1987 when he described the use of dilute lidocaine and epinephrine to permit liposuction totally by local anesthesia. The technique for tumescent local anesthesia is well known in dermatologic and plastic surgery literature. A detailed description of the tumescent technique has not been published in anesthesiology literature, and therefore, the unique benefits of the tumescent technique are not well recognized by anesthesiologists.

The tumescent technique comprises a drug delivery system that takes advantage of a recently discovered reservoir effect of injecting a relatively large volume of relatively dilute solution of a drug into the subcutaneous tissue.

The present invention takes advantage of the tumescent reservoir phenomenon for one of its important applications. After a large volume (e.g., multi liter) of fluid containing dilute epinephrine is injected into subcutaneous tissue, the epinephrine-induced vasoconstriction dramatically slows the systemic absorption of the fluid and minimizes surgical blood loss. In effect, this large volume of subcutaneous fluid behaves in a fashion that is analogous to the behavior of a slow-release tablet in the stomach after oral ingestion. Although there is a relatively large total amount of drug in the patient's body, the drug is isolated from the systemic circulation by the fact that only the drug on the outer boundary of the mass of drug is the available for absorption, whereas the portion of the drug located within the central portion of the mass of fluid is virtually isolated from the systemic circulation by virtue of profound capillary vasoconstriction. In contrast, when the tumescent fluid does not contain epinephrine there is no clinically significant vasoconstriction after tumescent infiltration, and the tumescent fluid is absorbed relatively rapidly. This has important clinical applications in situations where patients are hypovolemic or dehydrated and unable to be given fluids by mouth or intravenously. The tumescent technique permits rapid systemic hydration by direct subcutaneous or intramuscular injection of a large volume of fluid through a multi-fenestrated infiltration cannula described in this invention.

There is a prior art technique known as hypodermoclysis wherein a fluid is slowly and continuously infiltrated subcutaneously using a type of steel hypodermic needle, known as a butterfly needle, having a single distal aperture in order to provide fluid to patients who cannot be given fluids by mouth and for whom an IV access cannot be established. Typically hypodermoclysis is used in the treatment of infants, or cancer patients, in which IV access is not easily achieved. The technique of hypodermoclysis is typically used to deliver relatively small volumes of fluid, for example an adult might receive 70 ml per hour. At this small hourly volume hypodermoclysis is not an efficient method for the rapid systemic delivery of fluid in emergency situations that might require two to four liters per hour. The reason is that when using a cannula with only a single distal aperture, the local interstitial fluid pressure increases rapidly immediately adjacent to the single aperture as fluid infiltrates locally, which in turn dramatically slows the rate of subsequent fluid flow into the area. In contrast, the multiple apertures formed along the length of the cannula as described in the present invention, distribute the fluid throughout a much larger volume tissue before there can be a sufficient increase in the interstitial fluid to decrease the rate of additional infiltration. Also, the amount of pain is reduced because the rate of fluid flow through each of the apertures is less than the rate of fluid flow through the single aperture at the distal end. Further more, it is common practice to infiltrate the tumescent fluid into the subcutaneous space under augmented external pressure provided by an external peristaltic pump specifically designed for tumescent infiltration. By way of example and not limitation, a preferred suitable peristaltic infiltration pump is described in pending U.S. patent application Ser. No. 10/811,733, filed Mar. 29, 2004, entitled INFILTRATION PUMP HAVING INSULATED ROLLERS AND PROGRAMMABLE FOOT PEDAL, the disclosure of which is expressly incorporated herein by reference.

The peristaltic pump provides a sufficient degree of pressure to easily overcome the localized increased interstitial pressure associated with the local effects of a tumescent infiltration. On the other hand, in situations where a peristaltic infiltration pump is not available, such as in remote locations without any available electrical power, the present invention still permits relatively rapid tumescent infiltration by virtue of the multiple holes distributed along the length of the flexible cannula. Furthermore, external hydrostatic pressure can be applied to the fluid flowing into the flexible cannula from the fluid reservoir by means of gravitational force derived from elevating the reservoir one to two or more meters above the patient. When using gravity to augment the flow of tumescent fluid, the infiltration process can be continuous or intermittent. In exemplary embodiments, the intermittent injections are administered at intervals ranging from every few minutes to eight to twelve hours or more.

With the tumescent technique for local anesthesia, a large volume of dilute solution of local anesthesia and epinephrine is injected into the subcutaneous space resulting in a large bolus (or interstitial reservoir) of solution. The profound vasoconstrictive effect (shrinking of the capillaries) caused by the dilute epinephrine, produces a dramatic delay in the systemic absorption of the local anesthetic, which prolongs the anesthetic effects of tumescent anesthesia for eight to sixteen times longer than traditional techniques.

Figure 2:
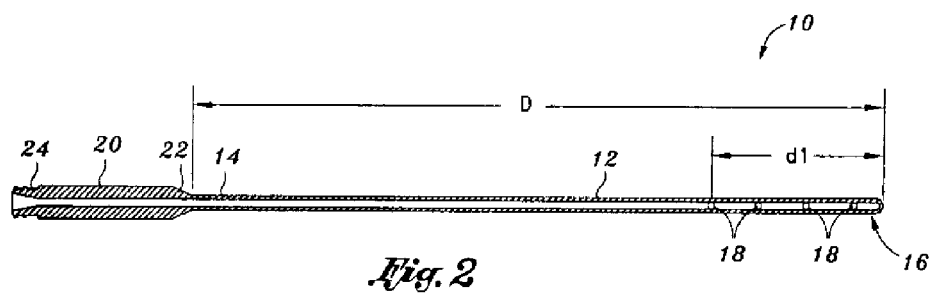
FIG. 2 is a section view of the infiltration cannula shown in FIG. 1.
Figure 3:
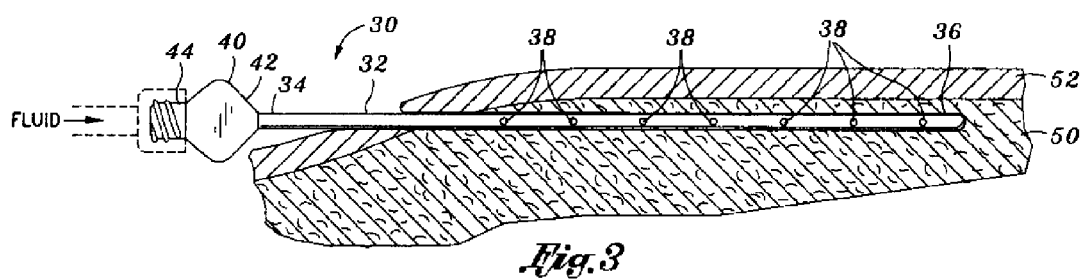
FIG. 3 is a side elevation view of a plastic infiltration cannula with a closed tip shown inserted in subcutaneous tissue shown in partial cross section.
Figure 4:
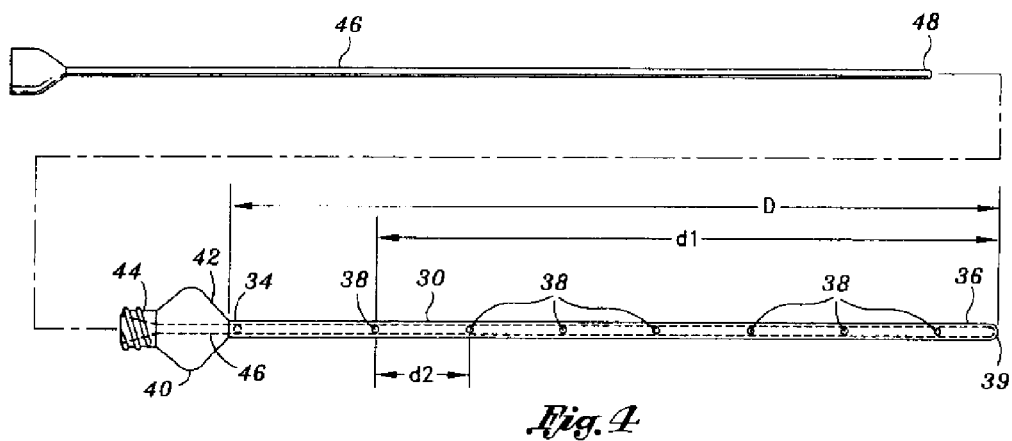
FIG. 4 is an exploded view of the infiltration cannula shown in FIG. 3 with a closed end.
Figure 6:
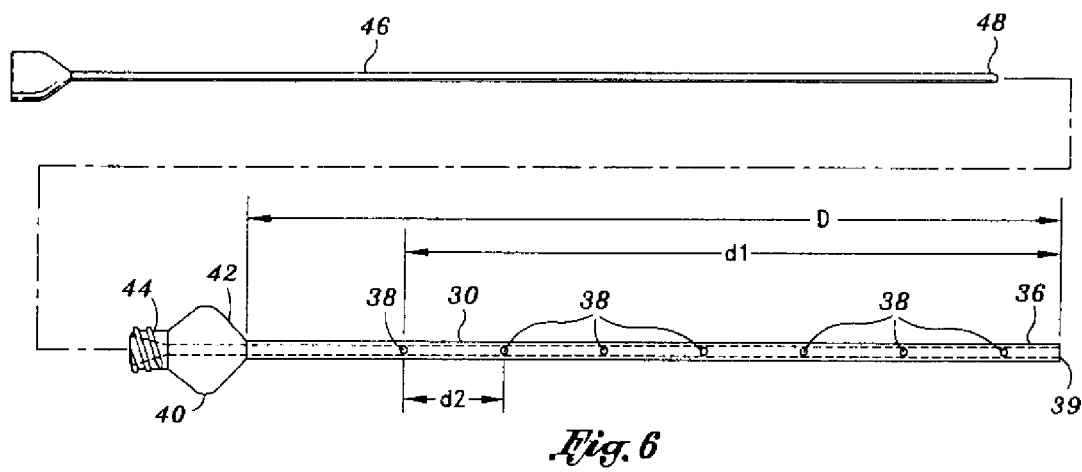
FIG. 6 is an exploded side elevation view of a plastic infiltration cannula through which a stylet can be inserted with an open end.

Referring now to the drawings wherein the showings are for purposes of illustrating preferred embodiments of the present invention only, and not for purposes of limiting the same, FIGS. 1 and 2 illustrate a stainless steel (reusable) infiltration cannula 10 and FIGS. 3-4 and 6 illustrate a (single use) plastic infiltration cannula 30. The cannula 10, 30 can be inserted under the skin 52 and into the subcutaneous tissue 50 and tumescent local anesthesia can be infiltrated either continuously until the clinical goal is achieved or intermittently (by way of example and not limitation, once every eight to twelve hours).

Stainless steel infiltration cannulas 10, such as the one shown in FIGS. 1 and 2, are formed having precision high quality and are preferably reusable. These cannulas can be used to provide tumescent local anesthesia for surgical procedures, such as liposuction, which require tumescent local anesthesia over a relatively large area.

The cannula 10 includes a tubular needle portion 12 which has a proximal end 14 and a distal end 16. The proximal end 14 of the tubular needle 12 is attached to a hub 20 that is used by the anesthesiologist or surgeon to grasp and hold the cannula 10 during the infiltration procedure. The hub 20 is connected to the tubular needle 12 at a first end 22 and has a connector 24, such as a luer lock, at an opposing second end. The connector 24 is connected to a fluid source, such as tubing connected to an IV bag. Fluid enters the cannula 10 via the connector 24.

In exemplary embodiments, the tip at the distal end 16 is closed. The local anesthetic is infiltrated into the patient via apertures 18 located proximate the distal end 16 of the tubular needle 12 of the cannula 10. It is contemplated that the apertures 18, 38 and 54 discussed herein may have a helical, spiral, linear or any random or ordered pattern. Also, in exemplary embodiments, the apertures 18 are disposed along the distal end 16 of the cannula 10 in a spiral or helical pattern and are distributed over the distal 33% to 100% of the tubular needle 12 of the cannula 10. For example, if the length of the tubular needle D is 15 cm and the apertures 18 at the distal end 16 cover a length d1 of 5 cm, the pattern of apertures of the cannula 10 are preferably distributed over 33% of the tubular needle 12 of the cannula 10. The size of the aperture and density of apertures on the tubular needle is limited by the structural integrity of the cannula. If the apertures 18 are too large or too close together then the cannula may bend or break during use (e.g., routine clinical applications). Prior art cannulas wherein the apertures are limited to the distal 25% of the cannula eject the fluid into the subcutaneous tissue at a high rate so as to cause discomfort to the patient. The apertures 18 which are located along a greater length of the cannula compared to prior art cannula allows fluid to flow out of each of the apertures at a slower rate but to achieve a greater amount of fluid flow as an aggregate so as to reduce the amount of discomfort to the patient due to the rate at which fluid flows out of each of the apertures. When tumescent fluid is injected into subcutaneous tissue, tumescent fluid spreads by means of simple bulk-flow through the interstitial gel substance. This process is extremely rapid and unimpeded by fibrous tissue.

The proximal portion 14 of the cannula 10 may be devoid of apertures in order to prevent fluid from leaking out of the cannula insertion site in the skin. Alternatively, if the proximal portion 14 of the cannula has aperture(s), then the hub may be used to prevent fluid from leaking out of the cannula insertion site in the skin in the follower manner. The hub of the infiltration cannula serves as a connector. The distal end of the hub attaches to the cannula, while the proximal end of the hub detachably connects to the plastic tube set which carries tumescent solution to the cannula. With a slight modification, the hub can also assist in reducing or virtually eliminating leakage of tumescent fluid out through the skin incision or adit site. An adit is a small round hole in the skin typically produced by a biosy punch. The hub 20 may have a conical configuration. The hub 20 may become narrower from the proximal end of the hub to the distal end of the hub. The rate at which the hub 20 becomes narrow may be less than about fifteen degrees with respect to a centerline of the hub. The outer surface of the hub 20 may have a plurality of rounded circular ridges equally spaced apart. The adit may be formed so as to have a diameter which is less than a diameter of the cannula or the outer surface of the hub. To minimize leakage of tumescent fluid out onto the surface of the skin, the cannula may initially be inserted into the adit. The adit is slightly stretched to accommodate the cannula. The cannula may be fully inserted into the subcutaneous tissue of the patient such that the distal end of the hub contacts the adit. The hub may then be pushed into the adit such that the inner diameter of the adit expands and slides over the rounded circular ridges formed on the distal end of the hub. The hub is gently wedged into the adit until there is a snug fit between the infiltration cannula and the adit. Leakage of fluid out of the adit may also be minimized by placing the proximal most aperture on the cannula sufficiently deep within the subcutaneous tissue such that fluid injected from the most proximal hole produces localized interstitial tumescence and a snug fit of the tissue against the cannula. It is also contemplated that the hub have other shapes such as curved, linear, parabolic, or combinations thereof.

Flexible plastic infiltration cannulas 30, such as the one shown in FIGS. 3, 4 and 6 are single use cannulas and can be used in one of several unique ways. First, an anesthesiologist, surgeon, untrained first responder, or even a victim can insert infiltration cannula 30 with stylet 46 into the subcutaneous tissue 50, remove the stylet 46, then attach an IV tubing to the infiltrator and inject tumescent local anesthesia or other tumescent fluid into the targeted area without subsequent repositioning of the infiltration cannula 30. The plastic flexible nature of the tubular needle 32 of the disposable plastic cannula 30 allows the patient to move or change position of the body without risk of injury that might result if a patient moves while a rigid steel cannula is inserted.

Preferably, the stylet 46 is formed of a rigid material such as metal, stainless steel, or plastic material. The stylet 46 should be sufficiently rigid so as to guide the tubular needle 32 of the cannula 30 into the subcutaneous tissue 50. The stylet 46 may be solid (see FIG. 4) or hollow (see FIG. 7) through its center. The plastic cannula 30 can be blunt-tipped with the metal stylet tip 48 covered by the rounded tip 39 of the plastic cannula 30, as shown in FIG. 4. Alternatively, the plastic cannula 30 can be open-ended with the stylet 46 extending a short distance past the end 39 of the plastic cannula 30 as shown in FIG. 6. In the case of the open ended cannula, the stylet 46 can be either blunt-tipped (see FIG. 6; requiring a skin incision to permit insertion into the subcutaneous space), or sharp-tipped (see FIG. 7; permitting the cannula to be inserted directly through the skin and into the subcutaneous space or muscle without requiring a preparatory skin incision). The sharp-tipped stylet 46 can be formed in either a solid (see FIG. 4) or hollow (see FIG. 7) cross-sectional configuration. The utility of a sharp tipped hollow stylet is that it can be inserted directly through the skin and then advanced painlessly through the subcutaneous tissue by slowly injecting local anesthetic solution through the stylet as it is slowly advanced, thereby anesthetizing the tissue in advance of the stylet's tip.

Figure 7:
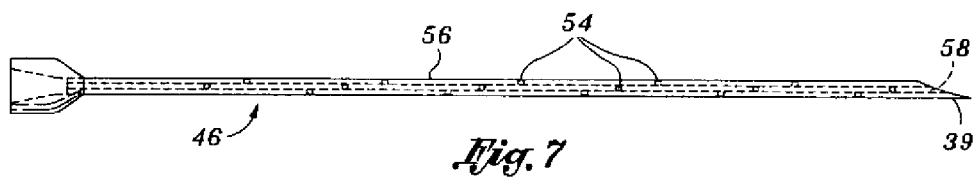
FIG. 7 is a side elevation view of a hollow sharp-tipped stylet with holes located along nearly the entire length of the stylet.

If the stylet 46 is hollow through its center 58, then apertures 54 may be formed along an entire length or along a portion (e.g., about 33% to 100%) of the length of the tubular needle 56 of the stylet 46, as shown in FIG. 7. The hollow stylet 46 (see FIG. 7) may be utilized in a similar fashion as the cannula 10 shown in FIGS. 1 and 2 and described herein. By way of example and not limitation, during use, the tubular needle 56 shown in FIG. 7 may be inserted into the cannula 30. The combined tubular needle 56 and cannula 30 may be inserted through the subcutaneous tissue 50 of the patient. The tubular needle 56 may be removed from the patient and the cannula 30. The tubular needle 56 of the stylet 46 may now be reinserted into the patient at a different site and used as a rigid cannula similar to the cannula 10 discussed in relation to FIGS. 1 and 2.

The stylet 46 shown in FIG. 7 has apertures 54 about the periperhy of tubular needle 56 of the stylet 46. The apertures 54 may have a pattern which is dissimilar to the pattern of apertures 38 formed in the tubular needle 32 of the cannula 30. Alternatively, the apertures 54 may have a pattern which is identical to the pattern of apertures 38 formed in the tubular needle 32 of the cannula 30. As a further alternative, some of the apertures 54 may have a pattern which is identical to the pattern of apertures 38 formed in the tubular needle 32 of the cannula 30. Also, some of the apertures 54 may have a pattern which is dissimilar to the pattern of apertures 38 formed in the tubular needle 32 of the cannula 30. During use, the medical professional may insert the stylet 46 (see FIG. 7) with apertures 54 into the cannula 30. The apertures 54 of the stylet 46 may be aligned or misaligned to the apertures 38 of the tubular needle by turning the stylet 46 within the cannula 30. The stylet 46 may have a hub with a similar configuration as hub 40. The hub of the stylet 46 may also be wedged into the adit of the patient to minimize or eliminate leakage of fluid, as discussed herein.

The plastic cannula shown in FIGS. 3 and 4 is similar to an IV catheter except the sharp hollow stylet used for the insertion of an IV catheter can be replaced by a solid obturator/stylet 46 that can be either sharp or blunt tipped. Except for the removable stylet 46, the plastic cannula 30 is similar to the stainless steel cannula 10 shown in FIGS. 1 and 2 and described above. The plastic cannula 30 includes a flexible tubular needle 32 having a proximal end 34 and a distal end 36. The distal end has apertures 38 and the proximal end 34 may be devoid of apertures. As stated above, in exemplary embodiments, the pattern of apertures 38 in the cannula 30 are distributed over the distal 33% to 100% (see FIG. 4) of the tubular needle 32 of the cannula 30. For example, if the tubular needle 32 of cannula 30 shown in FIGS. 3 and 4 has a length D of 15 cm and the pattern of apertures are distributed over a length d1 of 13.5 cm, then the apertures 38 are distributed over 90% of the cannula. As a further example, if the tubular needle 32 of cannula 30 shown in FIGS. 3 and 4 has a length D of 15 cm and the pattern of apertures are distributed over a length d1 of 15 cm, then the apertures 38 are distributed over 100% of the cannula. To stop leakage of tumescent fluid out of the adit site, the hub may be wedged into the adit site, as discussed above.

A typical infiltration cannula 10, 30 may have a diameter equivalent to 20, 18, 16 or 14 gauge with small apertures 18, 38 placed every 5 mm along the cannula in a spiral or helical pattern. The infiltration cannula 10, 30 may be 20-14 cm in length. A typical infiltration cannula 10, 30 is 15 cm or 20 cm in length. It will be appreciated that the dimensions used herein are exemplary and that the cannula dimensions, range of gauge, length range of cannula, relative size shape and pattern of apertures can vary greatly depending upon clinical preference.

The proximal end 34 of the tubular needle 32 shown in FIGS. 3 and 4 is attached to a hub 40 that is used by the anesthesiologist or surgeon to hold the cannula 30 during the infiltration procedure. The hub 40 is connected to the tubular needle 32 at a first end 42 and has a connector 44 at an opposing second end. The connector 44 is connected to a fluid source. As described above and shown in FIG. 4, the stylet 46 can be inserted and removed from the cannula 30.

Infiltration using a plastic infiltration cannula 30, such as the one shown in FIGS. 3 and 4, can be accomplished using an infiltration pump. Alternatively, the force of gravity could be used to push the tumescent fluid into the tissues by hanging a reservoir plastic bag of tumescent local anesthesia (or other dilute drug, such as a chemotherapeutic agent or antibiotics) on an IV pole and connecting bag to the infiltration cannula by an IV line.

Another application is the injection of tumescent local anesthesia into a localized area through which a surgeon plans to make a surgical incision. The effects of vasoconstriction, resulting from the epinephrine in the tumescent local anesthetic solution, within the tumesced tissue minimizes surgical bleeding. In a uniquely preemptive fashion, the present invention can produce, via the pre-operative infiltration of tumescent local anesthesia, prolonged post operative analgesia and also preemptively reduce the risk of surgical wound infections resulting from the bacteriacidal effects of lidocaine.

Lidocaine is bactericidal in vitro against *S. aureus*, and this effect increases with greater duration of exposure. In a dose-dependent fashion, clinical doses of lidocaine have been shown to inhibit the growth of bacterial pathogens commonly encountered in nosocomial wound infections. A tumescent epinephrine induces profound local vasoconstriction resulting in significantly delayed systemic absorption of a tumescent antimicrobial drug from subcutaneous tissue. In commercially available concentrations, the systemic absorption of an aqueous solution of lidocaine requires approximately 2 to 4 hours. In contrast, the systemic absorption of tumescent lidocaine requires 24 hours or more. Accordingly, a tumescent antibiotic can be expected to remain within the peri-incisional tissue at least 12 times longer than a routine aqueous antibiotic solution and the action would be far more effective. Moreover, a tiny hematoma within an incision may be an isolated avascular space and a potential nidus for an infection. The profound and prolonged vasoconstriction induced by tumescent epinephrine minimizes surgical bleeding and hematoma formation and therefore reduces the risk of SSI. Hypothermia is a major risk factor for postoperative SSI. Mild perioperative hypothermia, is common among patients having surgery under general anesthesia. The incidence of SSI was 5.8% in the normothermic (core body temperature 37 degrees C.) group and 18.8% in the hypothermic group (34.4 degrees C.) in a randomized, double blind trial. (Kurtz A, Sessler D I, Lenhardt R. Perioperative normothermia to reduce the incidence of surgical-wound infections and shorten hospitalization. Study of wound infection and temperature group. N Eng J Med 334:1209-15, 1996). Hypothermia also causes delays in moving the patient out of the recovery room. With surgery totally by tumescent local anesthesia there is no evidence of post operative hypothermia.

Infiltration of a tumescent solution containing lidocaine, epinephrine, and an antibiotic is likely to provide significantly improved SSI prophylaxis. Tumescent infiltration of antibiotics into peri-incisional skin and subcutaneous tissue offers the following advantages: prolonged local tissue concentrations of antibiotics, prolonged systemic delivery of antibiotic to tissues distant from the incision site, and significantly, the systemic absorption of tumescent lidocaine mimics IV delivery of lidocaine which is known to reduce postoperative pain and hasten post operative discharge from the hospital. The infiltration cannula discussed herein is the optimal device for tumescent delivery of antimicrobial drugs.

Yet another application is to provide an easily accessible route for systemic administration of crystalloid fluids/electrolytes for systemic hydration or for other types of drug therapy. Potential clinical applications include emergency resuscitation with systemic fluids in situations where insertion of an IV catheter into a vein cannot be readily achieved. Examples of situations where emergency access for intravenous delivery of fluids might not be possible include acute trauma or burn wound in civilian or military situations and very obese patients in which finding an accessible vein for IV access can be difficult even for a physician skilled in performing "IV cut-down" procedures. The infiltration cannula discussed herein may be a valuable adjunct to fluid resuscitation in an ambulance or an emergency room. Another application may be the emergency treatment of dehydration associated with pandemic influenza, prolonged vomiting or diarrhea as a result of chemical warfare or biological warfare (e.g., epidemic cholera among pediatric patients in rural third world settings) or other types of medical emergencies which overwhelm a medical center's capacity to care for incoming victims. A subcutaneous infiltration catheter can easily be introduced by a layman, whereas inserting an IV catheter into a vein of a patient that is severely dehydrated can be difficult even for a skilled physician. Delivery of systemic fluids by subcutaneous infiltration is safer than an IV infusion in a zero gravity situation (for example, the Space Station). The addition of a small amount of capillary vasodilator (e.g., methylnicotinamide) to the subcutaneous fluid can be used to accelerate the systemic absorption of the fluid or drug into the intravascular space. Further applicational uses for the present invention are described in co-pending application Ser. No. 10/877,337, filed Jun. 25, 2004, the disclosure of which is expressly incorporated herein by reference.

The continuos systemic drug delivery by tumescence has a similar therapeutic effect to continuous IV infusion but without the inherent expense, difficulties, and risk of an IV infusion. Compared to either oral delivery of a drug (inconsistent absorption from the gastrointestinal tract), or periodic intramuscular (IM) injections of a drug (variable serum concentrations), continuous systemic delivery is preferred in order to achieve prolonged and relatively uniform blood concentrations of the drug. This is especially true in critically ill patients. Tumescent delivery of a drug, placed in a tumescent solution containing epinephrine as a vasoconstrictor, produces a prolonged continuous system absorption of the drug over an interval of more than 24 hours. The simplicity and inexpensive equipment required to achieve continuous tumescent systemic drug delivery is clearly an advantage among medically impoverished populations, and in the demanding conditions of battlefield or at the scene of a mass casualty.

Yet another application is related to astronauts and systemic delivery of medication. In particular, the therapeutic options for treating an injured astronaut are limited. The fate of injured airplane pilots, passengers and astronauts are similar in that we presently have virtually no in-flight capability for treating an acute traumatic injury. If a pilot or astronaut survives the immediate effects of an explosion, burn, or decompression injury, or if there is an acute non-traumatic medical illness, it is assumed that the victim must return to terra firma for any significant therapeutic intervention such as providing systemic fluid replacement. The tumescent infiltrator is capable of providing systemic fluid and thus it is successfully solving a problem that has either never before been recognized, or has never before been solved by a simple device and technique.

The present invention allows improved emergency medical care for an injured astronaut on-board the ISS. Repeated and prolonged extra vehicular activities (EVA) expose astronauts to greater risk of physical trauma injury. Potential injury to astronauts include decompression injury-induced neurological injury and coma, acute pneumothorax, burns, and radiation injury. Assembly and maintenance of the ISS requires an unprecedented number of spacewalks, which expose astronauts to the risk of decompression sickness (DCS). In addition to humanitarian concerns, there is a strong economic incentive to provide on-board care for acute illness or trauma: the only alternative would be to abort an expensive mission and immediately return the victim to earth.

At present, there is no safe and easy means of providing the equivalent of IV fluids to a patient in space. Assuming there is a fellow astronaut with the requisite clinical skill to insert an intravenous (IV) catheter in a weightless environment, there is a problem of zero gravity. Whereas gravity separates air and water into distinct layers, in zero gravity there is a risk of air bubbles from the IV bag entering the IV line and causing intravascular air embolism. Because subcutaneous air is relatively safe, the tumescent infiltration cannula, by allowing effective systemic fluid resuscitation via subcutaneous infiltration, overcomes the above problems, and allows a person without clinical skills to safely provide the equivalent of IV fluids.

The cannula 10, 30 is intended to be inserted far enough through the skin 52 so that all of the apertures 18, 38 are within the fat 50 or muscle of the patient. If the apertures 18, 38 are distributed over about 100% of the cannula, the hub may be wedged into the adit to prevent or minimize leakage of the tumescent fluid out of the adit. Once the cannula 10, 30 is properly positioned, it can remain stationary while the local anesthetic (or other pharmaceutical) solution is injected. Since the cannula remains stationary, the associated pain or discomfort typically caused by the reciprocating in and out movement of prior art cannulas is reduced or eliminated. Accordingly, the cannula of the present invention permits infiltration of multi liter volumes of tumescent fluid into the patient in a safe and painless manner.

After one portion of the targeted area has been tumesced, the infiltration is briefly terminated (either by turning off the pump or by clamping the IV tubing) while the cannula 10, 30 is repositioned into another area of the subcutaneous tissue. Typically, the cannula is repositioned at the rate of about once per minute. The infiltration is then restarted with the cannula stationary in its new position. Since the apertures are distributed over the distal 33% to 100% of the cannula, the apertures distribute tumescent fluid into the patient along the entire length of cannula insertion. The cannula does not have to be reciprocated in and out to infiltrate the subcutaneous tissue like prior art cannula. Progressing repeatedly in this fashion, eventually all the fat within a targeted area becomes tumescent and profoundly anesthetic. As such, such method can obviate the need for general anesthesia or heavy IV sedation in most surgical procedures restricted to the skin and subcutaneous tissue.

The infiltrator 10, 30 can also be used in the traditional mode whereby the cannula 10, 30 is moved through the targeted tissue while the fluid is simultaneously pumped through the cannula 10, 30 and into the subcutaneous tissue 50.

Another unique aspect of the tumescent technique's reservoir effect is that one can conveniently achieve a long, slow, steady absorption of a drug delivered to the subcutaneous space 50 using periodic injections of a tumescent solution. In certain situations, using a slow IV infusion, the alternative technique, can achieve a slow systemic absorption of a drug but may be difficult, require greater clinical expertise, be more expensive, and therefore, less practical than the technique described herein.

Figure 5:
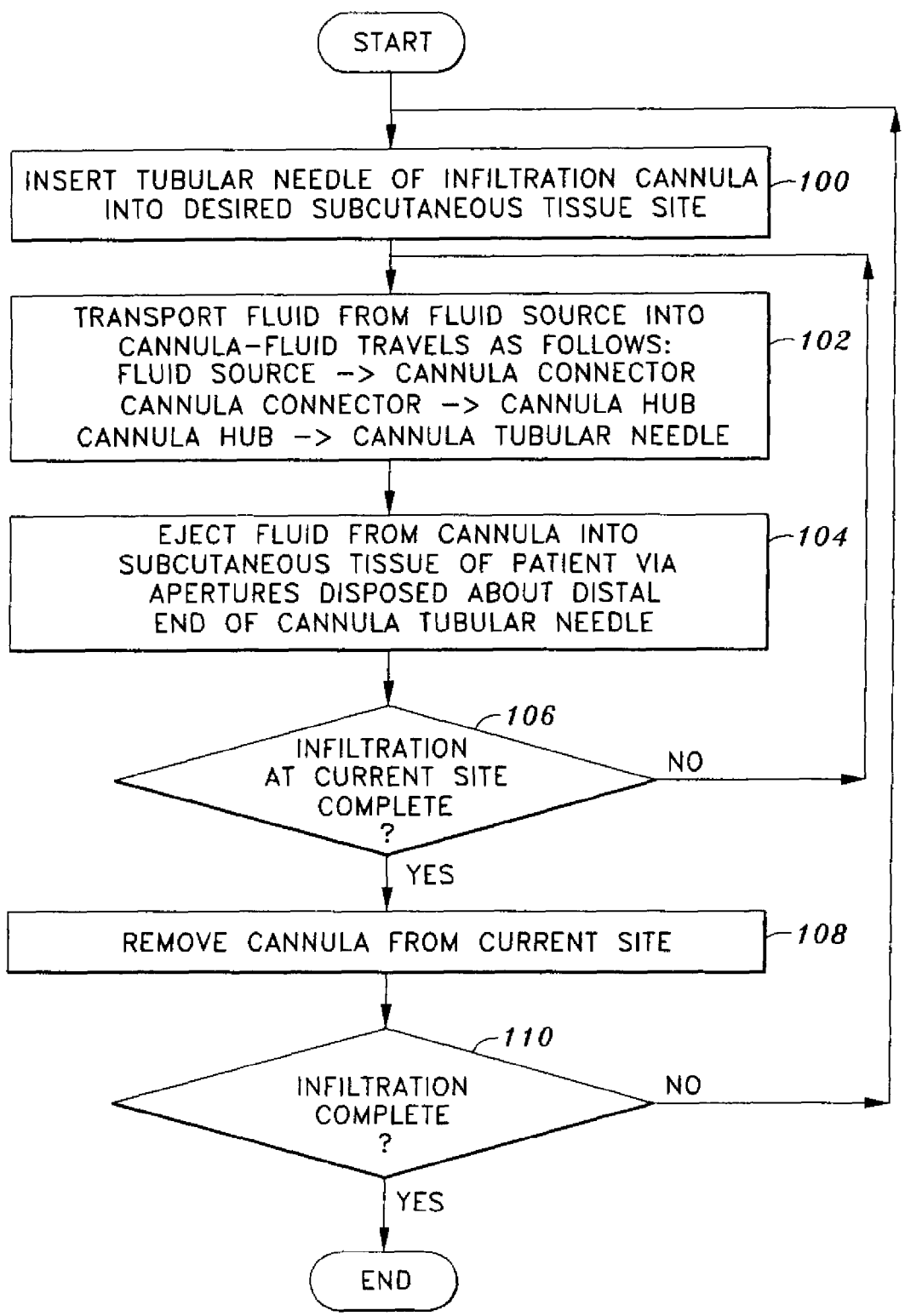
FIG. 5 is a flow diagram illustrating an exemplary procedure for using an infiltration cannula such as the one shown in FIG. 1 or the one shown in FIG. 3.

FIG. 5 is a flow diagram illustrating steps performed in an exemplary infiltration procedure using a cannula 10, 30 such as the one shown in FIGS. 1 and 2 or the one shown in FIGS. 3 and 4, respectively. The procedure begins by inserting the tubular needle 12, 32 of the infiltration cannula 10, 30 into a desired subcutaneous tissue site 50, e.g., via an incision in the patient's skin 52 (block 100). Fluid is then transported from the fluid source (e.g., an IV bag) into the cannula 10, 30 via the connector 24, 44 that is connected to the fluid source. The fluid is transported from the connector 24, 44 through the hub 20, 40 and into the tubular needle 12, 32 (block 102). The fluid is then ejected from the cannula 10, 30 into the subcutaneous tissue 50 of the patient via the apertures 18, 38 at the distal end 16, 36 of the tubular needle 12, 34 of the cannula 10, 30 (block 104).

The fluid is transported (block 102) and ejected (block 104) until infiltration at the current site is completed (yes in decision block 106). Complete infiltration at the current site may take approximately one or two minutes. The fluid can be injected into multiple sites in order to distribute the solution over a greater area.

Infiltration at a particular site may be deemed complete upon emptying of the fluid source or based on the anesthesiologist or surgeon's decision to stop the infiltration at the current site. After one portion of the targeted area has been tumesced, the infiltration can be briefly terminated (either by turning off the pump or by clamping the IV tubing) while the cannula 10, 30 is repositioned into another area of the subcutaneous tissue. The infiltration may then be restarted with the cannula stationary in its new position. If the infiltration at a site is complete (yes in decision block 106), the cannula is removed from the current site (block 108). If the infiltration at the current site is not complete (no in decision block 106), fluid is transported from the fluid source (block 102) and ejected into the subcutaneous tissue (block 104) until infiltration at the site is complete (yes in decision block 106).

If infiltration is complete at the current site (yes in decision block 106) but infiltration is not complete (no in decision block 110), the tubular needle 12, 32 of the infiltration cannula 10, 30 is inserted into a new area of subcutaneous tissue 50. By way of example and not limitation, the tubular needle 12, 32 may be inserted into a new area adjacent the current site. The adjacent site may be partially anesthetized by infiltration of the anesthetic solution at the current site. As such, pain to the patient caused by insertion of the tubular needle 12, 32 is minimized, eliminated or greatly reduced. The process described above is performed until the infiltration process is complete (yes in decision block 110). This process can be continuous or repeated intermittently. It is contemplated that infiltration of up to about 50% of the patient's body may be achieved in the manner described herein.

As described above, multiple infiltration cannulas (e.g., can be used at once). Thus, a second or additional cannulas can be inserted (block 100) at the same time as a first cannula is being removed (block 108). For example, the second cannula may be inserted parallel to the first cannala and into an area immediately adjacent to the area in which the first cannula is inserted. In this manner, the pain usually associated with the insertion of the cannula into the patient's fat tissue is reduced or eliminated because the first cannula has already at least partially anesthetized the area in which the second cannula is inserted. The second cannula is positioned adjacent the first cannula approximately every one or two minutes. The first cannula may then be removed from the patient's body after the second cannula is inserted. Moreover, the infiltration process need not be interrupted in order to reposition a single cannula. Progressing repeatedly in this fashion, eventually all the fat within a targeted area becomes tumescent and profoundly anesthetic. As such, such method can obviate the need for general anesthesia or heavy IV sedation.

The plastic infiltration cannula shown in FIGS. 3 and 4 may be used by either a lay person or a clinical professional for the delivery of tumescent fluid for either tumescent local anesthesia, tumescent antimicrobial therapy, or emergency delivery of systemic fluids by tumescent infiltration. In an aspect of the cannulas 10, 30, it is contemplated that such cannulas 10, 30 may be utilized for continuous systemic tumescent delivery of a drug which produces a continuos system absorption of the drug over nearly 24 hours in a fashion similar to a continuous IV infusion.

The infiltration cannula 10, 30 discussed herein is a subcutaneous device and not an intravascular device for infiltration of multi-liter volumes of fluid into areas of up to 50% of the total body surface area. For example, the infiltration cannulas 10, 30 infiltrates approximately 1,000 times the volume of fluid delivered by the Schwartz device discussed in the background.

Additional modifications and improvements of the present invention may also be apparent to those of ordinary skill in the art. Thus, the particular combination of parts described and illustrated herein is intended to represent only a certain embodiment of the present invention, and is not intended to serve as a limitation of alternative devices within the spirit and scope of the invention.

What is claimed is:

1. A method of minimizing infections at a surgical site, the method comprising the steps of:
    providing a solution containing an antibiotic and a vasoconstrictive drug;
    inserting a tubular needle having apertures into an adit of the patient such that the tubular needle is adjacent the surgical site to infiltrate the solution at the surgical site;
    flowing the antibiotic/vasoconstrictive drug solution through the tubular needle and out of the apertures to constrict the blood vessels and delay systemic absorption of the antibiotic for prolonging a length of time that the antibiotic remains at the surgical site; and
    performing surgery at the surgical site wherein a first surgical incision is made after a period of time has elapsed for the antibiotic/vasoconstrictive drug solution has permeated the surgical site during the flowing step.

2. The method of claim 1 further comprising the step of mixing lidocaine into the antibiotic/vasoconstrictive drug solution for providing an antibacterial effect.

* * * * *